United States Patent
Druzgala et al.

(10) Patent No.: US 6,951,877 B2
(45) Date of Patent: Oct. 4, 2005

(54) MATERIALS AND METHODS FOR TREATING HYPERCHOLESTEROLEMIA

(75) Inventors: Pascal Druzgala, Santa Rosa, CA (US); Xiaoming Zhang, Campbell, CA (US)

(73) Assignee: ARYx Therapeutics, Inc., Fremont, CA (US)

(*) Notice: Subject to any disclaimer, the term of this patent is extended or adjusted under 35 U.S.C. 154(b) by 0 days.

(21) Appl. No.: 10/624,659

(22) Filed: Jul. 21, 2003

(65) Prior Publication Data

US 2004/0068001 A1 Apr. 8, 2004

Related U.S. Application Data

(60) Provisional application No. 60/397,076, filed on Jul. 19, 2002.

(51) Int. Cl.⁷ ................................................ A61K 31/44
(52) U.S. Cl. .................. 514/356; 514/277; 546/318; 546/342
(58) Field of Search ................... 546/170, 173, 546/318, 342; 514/277, 311, 356

(56) References Cited

U.S. PATENT DOCUMENTS 5,849,749 A  * 12/1998  Fey et al. .................... 514/277

FOREIGN PATENT DOCUMENTS

| EP | 0 464 817 A | 1/1992 |
| WO | WO 01 81328 A | 11/2001 |
| WO | WO 01 85975 A | 11/2001 |
| WO | WO 02 24689 A | 3/2002 |

* cited by examiner

*Primary Examiner*—Amelia Averill Owens
(74) *Attorney, Agent, or Firm*—McDonnell Boehnen Hulbert & Berghoff LLP

(57) ABSTRACT

The subject invention provides novel HMG-CoA-reductase inhibitors. In a preferred embodiment, the HMG-CoA reductase inhibitors of the subject invention can be deactivated to a primary inactive metabolite by hydrolytic enzymes. Compounds of the present invention can be advantageously used to treat patients suffering hypercholesterolemia.

10 Claims, 4 Drawing Sheets

Pravastatin

Simvastatin

Lovastatin

Fluvastatin

Cerivastatin

Atorvastatin n=1-3

MATERIALS AND METHODS FOR TREATING HYPERCHOLESTEROLEMIA

CROSS-REFERENCE TO RELATED APPLICATION

This application claims the benefit of U.S. Provisional Application No. 60/397,076, filed Jul. 19, 2002.

BACKGROUND OF INVENTION

Elevated levels of low-density lipoprotein (LDL)-cholesterol has been recognized as the most important risk factor for Coronary Artery Disease (CAD). The most effective method of LDL-cholesterol lowering is the administration of inhibitors of HMG-CoA reductase (statins), a rate-limiting key enzyme of the cholesterol synthesis pathway. Since the discovery of compactin and lovastatin, both of which were compounds of microbial origin, primary and secondary preventive measures have been established in several statin trials to help prevent future events of CAD by lowering LDL-cholesterol levels. To date, pravastatin, lovastatin, simvastatin, fluvastatin, cerivastatin and atorvastatin have been used in clinical practice.

Several landmark studies demonstrate that primary and secondary prevention strategies with lipid-lowering therapies provide significant reductions in cardiovascular morbidity and mortality. The Helsinki Heart Study demonstrated the benefit of lipid lowering in asymptomatic, middle-aged men with primary hypercholesterolemia. Treatment with gemfibrozil increased HDL cholesterol and lowered LDL, cholesterol; this improved lipid profile was associated with a significant 34% reduction in CHD risk over the 5-year follow-up period.

The Scandinavian Simvastatin Survival Study (4S) and the Cholesterol and RecurrentEvents (CARE) trial demonstrated the benefit of lipid lowering with statins in patients with established CAD. In 4S, simvastatin treatment reduced LDL cholesterol by 35% and increased HDL cholesterol by 8%. This was associated with significant 30% and 42% reductions in all-cause and coronary mortality risk, respectively, and a 34% reduction in major coronary events over the mean 5.4-year follow-up period. In the CARE study, pravastatin significantly reduced risk, for fatal coronary events or nonfatal MI by 24% over a 5-year period. Taken together, these studies demonstrate that a reduction in LDL cholesterol of approximately 25%–35% significantly reduces risk for cardiovascular morbidity and mortality in patients with or without established CAD.

Several recent studies using quantitative coronary angiography demonstrate that lipid lowering slows progression of coronary atherosclerosis in CAD patients. In the Lipoprotein and Coronary Atherosclerosis Study (LCAS), fluvastatin was administered to patients with angiographic CAD who had baseline LDL cholesterol levels of 115–190 mg/dL. Fluvastatin reduced LDL cholesterol by 24% and significantly reduced progression of coronary atherosclerosis over the 2.5-year follow-up period. In the Pravastatin Limitation of Atherosclerosis in the Coronary Artery (PLAC I) study, pravastatin was administered to CAD patients with baseline LDL cholesterol levels of 130–190 mg/dL. Pravastatin significantly reduced LDL cholesterol by 28% and atherosclerotic progression by 40% over the 3-year follow-up. As coronary atherosclerosis progresses, interventional procedures, such as balloon angioplasty, must be performed to reduce cardiac risk. Therefore, the Atorvastatin Versus Revascularization Treatments (AVERT) study was designed to ascertain if aggressive lipid lowering with atorvastatin can be used as an alternative to angioplasty or other catheter-based revascularization procedures in patients with significant CAD. The primary end point in this ongoing 18-month, open-label trial is the incidence of ischemic events.

The statins, in general are well tolerated during long-term use as evidenced by results from the major outcomes studies. The most serious adverse event associated with statins is myopathy, which occurs in 0.2% or less of treated patients. Myopathy is characterized by myalgia, muscle tenderness and weakness, and marked elevation in creatine phosphokinase to 10 or more times the upper limits of normal (ULN). In rare cases, myopathy may progress to rhabdomyolysis with acute renal failure. Risk for myopathy and rhabdomyolysis is increased by concomitant use of statins with gemfibrozil, cyclosporine, erythromycin, niacin, or azole antifungal agents. In approximately 1%–2% of patients, statins cause persistent elevations in liver function enzymes that are 3 times greater than the ULN. The incidence of elevated liver enzymes increases with higher statin doses. For example, during clinical trials with atorvastatin, elevated liver enzymes were found in 0.2% of patients receiving doses of 10 or 20 mg, 0.6% of those receiving 40 mg, and 2.3% of those receiving 80 mg. In general, a reduction in dose or discontinuation of statin treatment results in the return of liver enzymes to baseline levels.

While all statins have been associated with very rare reports of rhabdomyolysis, cases of fatal rhabdomyolysis in association with the use of cerivastatin have been reported significantly more frequently than for other approved statins. Fatal rhabdomyolysis reports with cerivastatin have been reported most frequently when used at higher doses, when used in elderly patients, and particularly, when used in combination with gemfibrozil (LOPID and generics), another lipid lowering drug. FDA has received reports of 31 U.S. deaths due to severe rhabdomyolysis associated with use of cerivastatin, 12 of which involved concomitant gemfibrozil use.

The rare rhabdomyolysis is presumed to be the result of higher level of systemic exposure of statins. Therefore HMG-CoA-reductase inhibitors with high first-pass metabolism and/or short plasma half-life would be desirable, since they will have limited systemic exposure and more predictable metabolic profile.

BRIEF SUMMARY

The subject invention provides new and advantageous materials and methods for treating hypercholesterolemia. The compositions and therapeutic methods of the subject invention can be used to effectively and safely reduce cholesterol levels. Specifically exemplified herein are novel inhibitors of HMG-CoA reductase. The use of these compounds helps to prevent Coronary Artery Disease (CAD) by lowering LDL cholesterol levels.

The compounds of the subject invention are particularly advantageous because of their favorable metabolic profile. Specifically, these compounds are readily metabolized by hydrolytic enzymes. Thus, these compounds which have a highly predictable pharmokinetic profile are particularly advantageous because they reduce systemic exposure to the active drug.

The present invention also provides methods of treatment which involve administering an effective amount of a compound of the present invention to a person in need of such treatment.

BRIEF DESCRIPTION OF DRAWINGS

FIG. 4(a) NaH, BuLi, cinnamaldehyde (b) NaBH$_4$, triethylborane (c) Acetone dimethylacetal, H$^+$ (d) OsO$_4$/NaIO$_4$. FIG. 5(a) NaBH$_4$ (b) RCOCl/Triethylamine (c) H$_2$, Pd/C, then H$^+$. FIG. 6(a) PDC/DMF (b) ROH/DCC (c) H$_2$, Pd/C, then H$^+$.

DETAILED DISCLOSURE

The subject invention provides novel HMG-CoA-reductase inhibitors. In a preferred embodiment, the HMG-CoA reductase inhibitors of the subject invention can be deactivated to a primary inactive metabolite by hydrolytic enzymes. Compounds of the present invention can be advantageously used to treat individuals suffering hypercholesterolemia. The compounds of the subject invention are particularly advantageous because they have more predictable pharmacokinetics and reduced systemic exposure of the drugs.

As used herein, the term "individual(s)" refers to a mammal to which is administered a compound or composition of the present invention. The mammal may be, for example a mouse, rat, pig, horse, rabbit, goat, pig, cow, cat, dog, or human. In a preferred embodiment, the individual is a human.

Figure 1A:
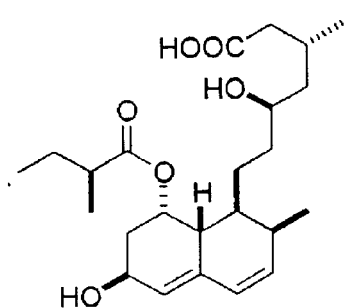
FIGS. 1A–1F shows the structures of various compounds currently used for lowering cholesterol levels.
Figure 1B:
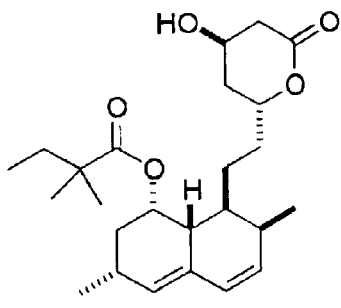
Figure 1C:
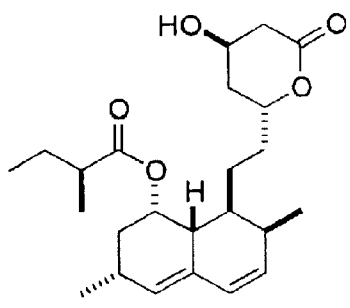
Figure 1D:
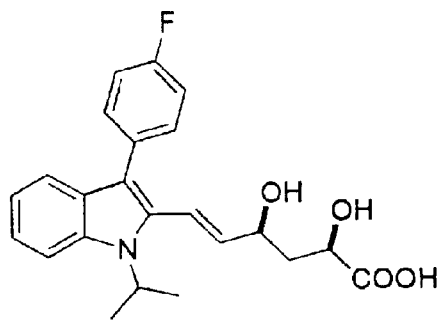
Figure 1E:
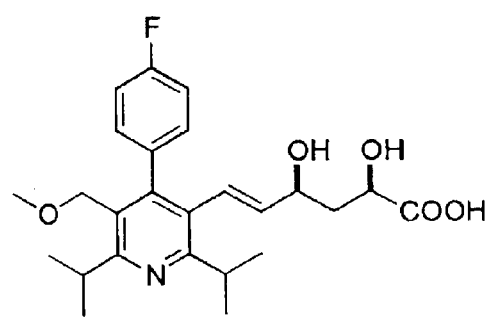
Figure 1F:
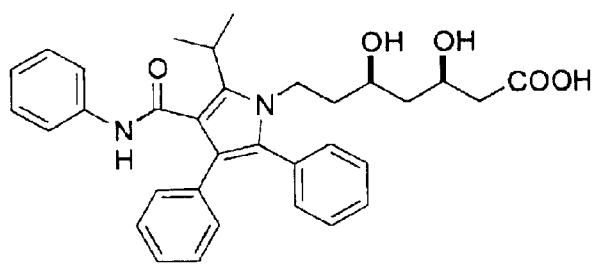
Figure 2A:
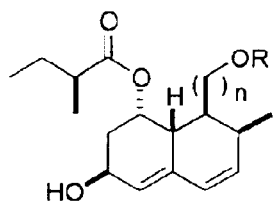
FIGS. 2A–2N shows specific compounds of the subject invention.
Figure 2B:
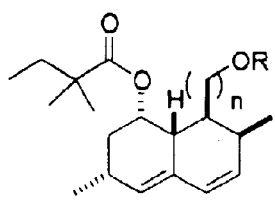
Figure 2C:
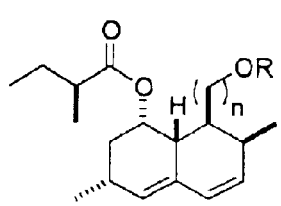
Figure 2D:
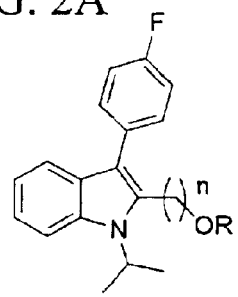
Figure 2E:
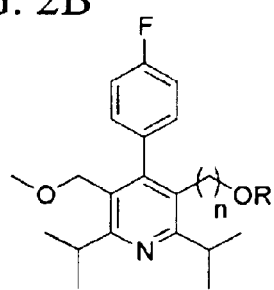
Figure 2F:
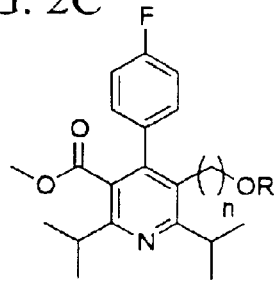
Figure 2G:
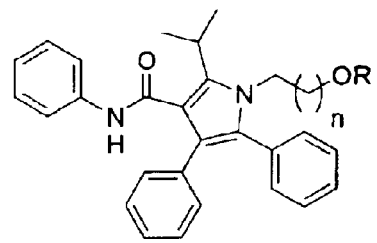
Figure 2H:
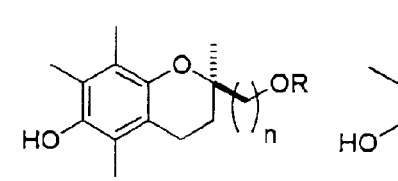
Figure 2I:
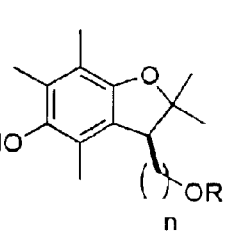
Figure 2J:
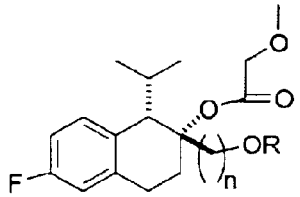
Figure 2K:
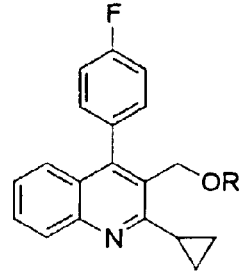
Figure 2L:
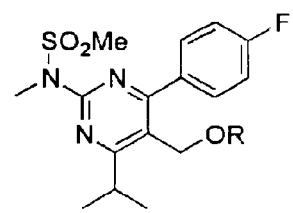
Figure 2M:
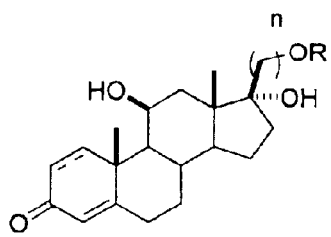
Figure 2N:
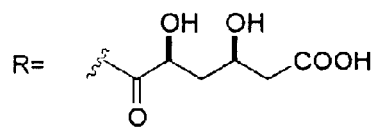
Figure 3A:
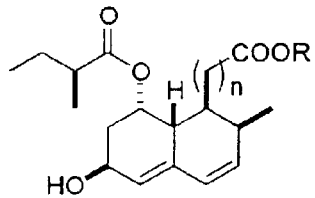
FIGS. 3A–3N shows specific compounds of the subject invention.
Figure 3B:
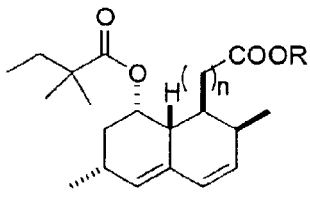
Figure 3C:
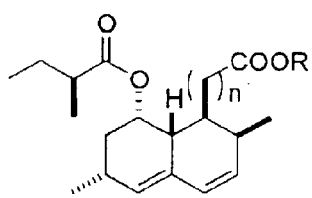
Figure 3D:
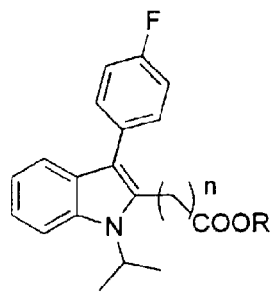
Figure 3E:
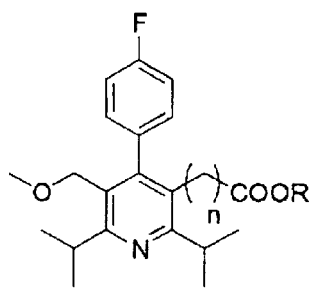
Figure 3F:
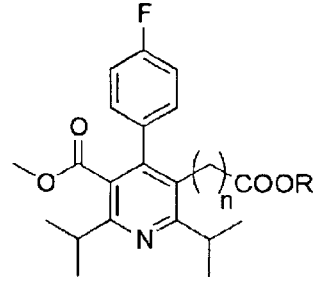
Figure 3G:
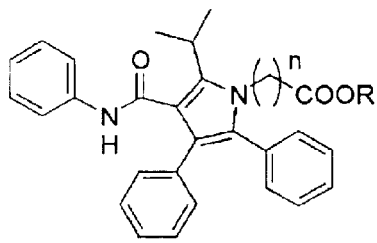
Figures 3H, 3I:
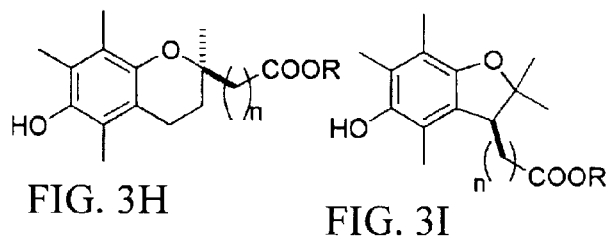
Figure 3J:
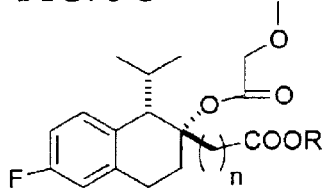
Figure 3K:
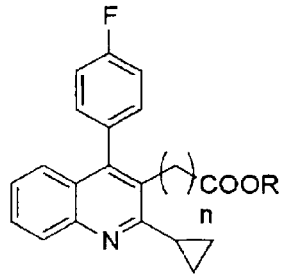
Figure 3L:
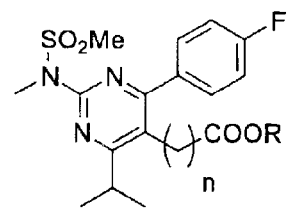
Figure 3M:
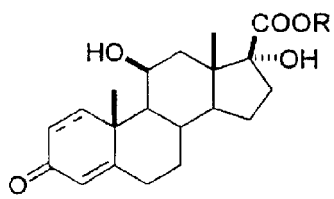
Figure 3N:
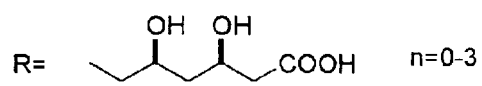
Figure 4:
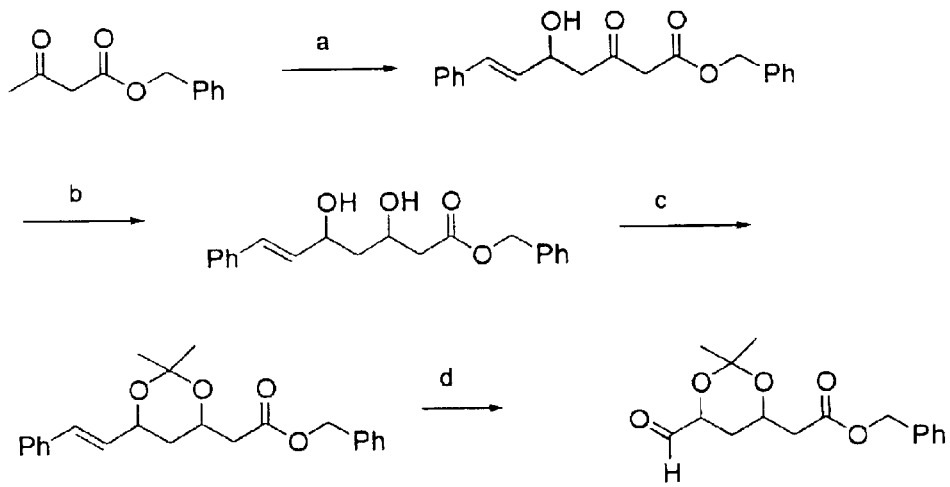
FIGS. 4–6 provide examples of synthesis procedures which can be used to produce compounds of the subject invention.
Figure 5:
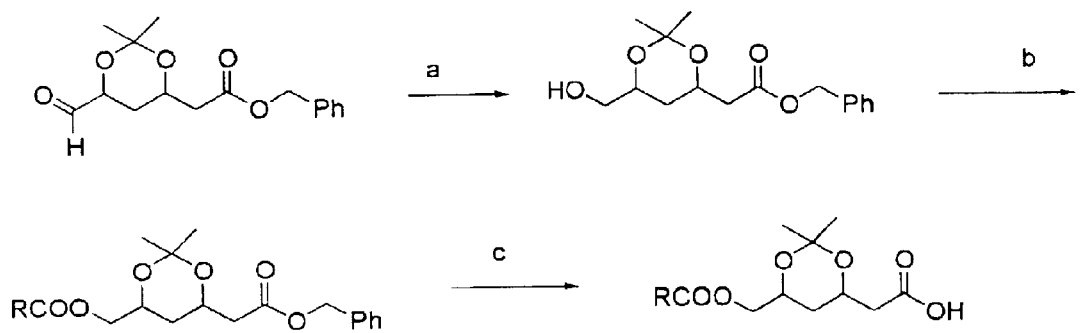
Figure 6:
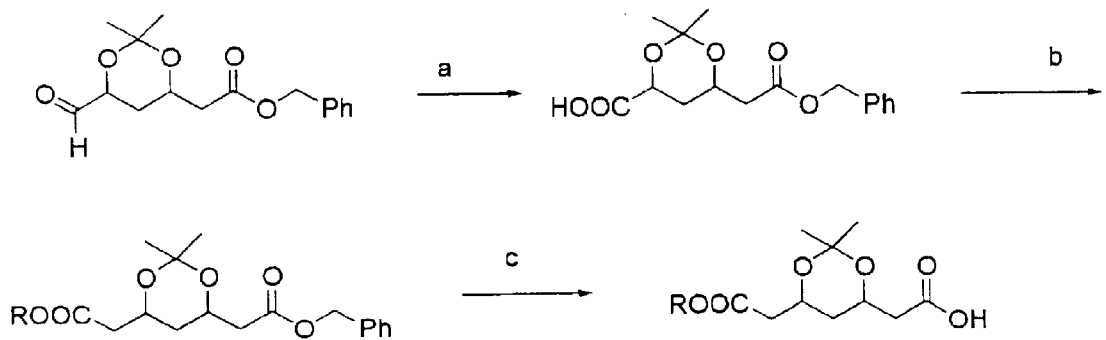

Lovastatin, pravastain, simvastatin, atorvastatin, cerivastatin and fluvastatin are widely used for treating hypercholesterolemia (FIGS. 1A–1F). The present invention provides novel statin analogues that are preferentially metabolized by endogenous hydrolytic enzymes (FIGS. 2A–2N and FIGS. 3A–3N). The novel compounds are bioactive molecules having antilipidemic properties and which undergo deactivation to primary inactive metabolites by hydrolytic enzymes. FIGS. 4–6 provide examples of synthesis procedures which can be used to produce compounds in the subject invention.

Adverse drug-drug interactions (DDI), elevation of liver function test (LFT) values, and QT prolongation leading to torsades de pointes (TDP) are three major reasons why drug candidates fail to obtain FDA approval. All these causes are, to some extent, metabolism-based. A drug that has two metabolic pathways, one oxidative and one non-oxidative, built into its structure is highly desirable in the pharmaceutical industry. An alternate, non-oxidative metabolic pathway provides the treated subject with an alternative drug detoxification pathway (an escape route) when one of the oxidative metabolic pathways becomes saturated or non-functional. While a dual metabolic pathway is necessary in order to provide an escape metabolic route, other features are needed to obtain drugs that are safe regarding DDI, TDP, and LFT elevations.

In addition to having two metabolic pathways, the drug should have a rapid metabolic clearance (short metabolic half-life) so that blood levels of unbound drug do not rise to dangerous levels in cases of DDI at the protein level. Also, if the metabolic half-life of the drug is too long, then the CYP450 system again becomes the main elimination pathway, thus defeating the original purpose of the design. In order to avoid high peak concentrations and rapidly declining blood levels when administered, such a drug should also be administered using a delivery system that produces constant and controllable blood levels over time.

The compounds of this invention have one or more of the following characteristics or properties:

1. Compounds of the invention are metabolized both by CYP450 and by a non-oxidative metabolic enzyme or system of enzymes;

2. Compounds of the invention have a short (up to four (4) hours) non-oxidative metabolic half-life;

3. Oral bioavailability of the compounds is consistent with oral administration using standard pharmaceutical oral formulations; however, the compounds, and compositions thereof, can also be administered using any delivery system that produces constant and controllable blood levels over time;

4. Compounds according to the invention contain a hydrolysable bond that can be cleaved non-oxidatively by hydrolytic enzymes;

5. Compounds of the invention can be made using standard techniques of small-scale and large-scale chemical synthesis;

6. The primary metabolites of compounds of this invention results from the non-oxidative metabolism of the compounds;

7. The primary metabolites, regardless of the solubility properties of the parent drug, is, or are, soluble in water at physiological pH and have, as compared to the parent compound, a significantly reduced pharmacological activity;

8. The primary metabolites, regardless of the electro-physiological properties of the parent drug, has, or have, negligible inhibitory activity at the IK$_R$ (HERG) channel at normal therapeutic concentration of the parent drug in plasma (e.g., the concentration of the metabolite must be at least five times higher than the normal therapeutic concentration of the parent compound before activity at the IK$_R$ channel is observed);

9. Compounds of the invention, as well as the metabolites thereof, do not cause metabolic DDI when co-administered with other drugs;

10. Compounds of the invention, as well as metabolites thereof, do not elevate LFT values when administered alone.

In some embodiments, the subject invention provides compounds having any two of the above-identified characteristics or properties. Other embodiments provide for compounds having at least any three of the above-identified properties or characteristics. In another embodiment, the compounds, and compositions thereof, have any combination of at least four of the above-identified characteristics or properties. Another embodiment provides compounds have any combination of five to 10 of the above-identified characteristics or properties. In a preferred embodiment the compounds of the invention have all ten characteristics or properties.

In various embodiments, the primary metabolites of the inventive compounds, regardless of the electrophysiological properties of the parent drug, has, or have, negligible inhibitory activity at the IK$_R$ (HERG) channel at normal therapeutic concentrations of the drug in plasma. In other words, the concentration of the metabolite must be at least five times higher than the normal therapeutic concentration of the parent compound before activity at the IK$_R$ channel is observed. Preferably, the concentration of the metabolite must be at least ten times higher than the normal therapeutic concentration of the parent compound before activity at the IK$_R$ channel is observed.

Compounds according to the invention are, primarily, metabolized by endogenous hydrolytic enzymes via hydrolysable bonds engineered into their structures. The primary metabolites resulting from this metabolic pathway are water soluble and do not have, or show a reduced incidence of, DDI when administered with other medications (drugs). Non-limiting examples of hydrolysable bonds that can be incorporated into compounds according to the invention include amide, ester, carbonate, phosphate, sulfate, urea, urethane, glycoside, or other bonds that can be cleaved by hydrolases.

Additional modifications of the compounds disclosed herein can readily be made by those skilled in the art. Thus, analogs and salts of the exemplified compounds are within the scope of the subject invention. With a knowledge of the compounds of the subject invention skilled chemists can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound.

The subject invention further pertains to enantiomerically isolated compounds, and compositions comprising the compounds, for inhibition of HMG-CoA-reductase. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least 99% enantiomeric excess.

A further aspect of the subject invention pertains to the breakdown products which are produced when the therapeutic compounds of the subject invention are acted upon by hydrolytic enzymes, such as esterases. The presence of these breakdown products in urine or serum can be used to monitor the rate of clearance of the therapeutic compound from a patient.

The compounds of this invention have therapeutic properties similar to those of the unmodified parent compounds. Accordingly, dosage rates and routes of administration of the disclosed compounds are similar to those already used in the art and known to the skilled artisan (see, for example, *Physicians' Desk Reference*. 54$^{th}$ Ed., Medical Economics Company, Montvale, N.J., 2000).

The compounds of the subject invention can be formulated according to known methods for preparing pharmaceutically useful compositions. Formulations are described in detail in a number of sources, which are well known and readily available to those skilled in the art. For example, *Remington's Pharmaceutical Science* by E. W. Martin describes formulation, which can be used in connection with the subject invention. In general, the compositions of the subject invention are formulated such that an effective amount of the bioactive compound(s) are present in the composition.

In accordance with the subject invention, pharmaceutical compositions are provided which comprise, as an active ingredient, an effective amount of one or more of the compounds and one or more non-toxic, pharmaceutically acceptable carriers or diluents.

Compounds of the present invention may be formulated as solutions or suspensions, in the form of tablets, capsules (each including timed release and sustained release formulations), pills, oils, powders, granules, elixers, tinctures, suspensions, syrups, emulsions, microemulsions, or with excipients. Likewise, they may also be administered by any conventional route, for example in intravenous (both bolus and infusion), intraperitoneal, intraocularly, subcutaneous, intramuscular form, enterally, preferably orally (e.g., in the form of tablets or capsules), or in a nasal, buccal, transdermal, or a suppository form, using well known formulations to those of ordinary skill in the pharmaceutical arts.

In addition, the compounds of the present invention can also be administered in the form of liposomes or the like. Disintegrators include, without limitation, delivery systems such as small unilamellar vesicles, large unilamellar vesicles and multilamellar vesicles. Liposomes can be formed from a variety of phospholipids, such as cholesterol, stearylamine or phosphatidylcholines.

For oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, for example, sodium oleate, sodium stearate, magnesium stearate, sodium benzoate, sodium acetate, sodium chloride, starch, methyl cellulose, agar, bentonite, zanthan gum, and the like.

The dosage regimen for the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

In general, satisfactory results in animals are indicated to be obtained at a daily dosage of from about 0.1 to about 200 mg, preferably from about 0.1 to about 5 mg/kg animal body weight. In larger mammals, for example humans, an indicated daily dosage is in the range from about 0.5 to about 100 mg, preferably from about 1 to about 50 mg of an agent of the invention conveniently administered, for example, in divided doses up to four times a day or in sustained release form.

Injected intravenous, subcutaneous or intramuscular dosages of the compounds of the present invention, when used for the indicated effects, will range between about 0.001 to 1.0 mg/kg. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Transdermal delivery can also be achieved using approaches known to those skilled in the art.

The subject invention further provides methods of synthesizing the unique and advantageous therapeutic compounds of the subject invention. Particularly, methods of producing less toxic therapeutic agents comprising introducing ester groups into therapeutic agents are taught. The ester linkage may be introduced into the compound at a site which is convenient in the manufacturing process for the compounds of the invention. Various exemplary synthetic routes for the preparation of the compounds of the subject invention are described. Additionally, the sensitivity of the ester linkage may be manipulated by the addition of side groups which hinder or promote the hydrolytic activity of the hydrolases or esterases responsible for cleaving the drug at the ester locus. Methods of adding such side groups, as well as the side groups themselves, are well known to the skilled artisan and can be readily carried out utilizing the guidance provided herein.

All patents, patent applications, provisional applications, and publications referred to or cited herein are incorporated by reference in their entirety to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. An inhibitor of HMG-CoA reductase having a structure selected from the group consisting of:

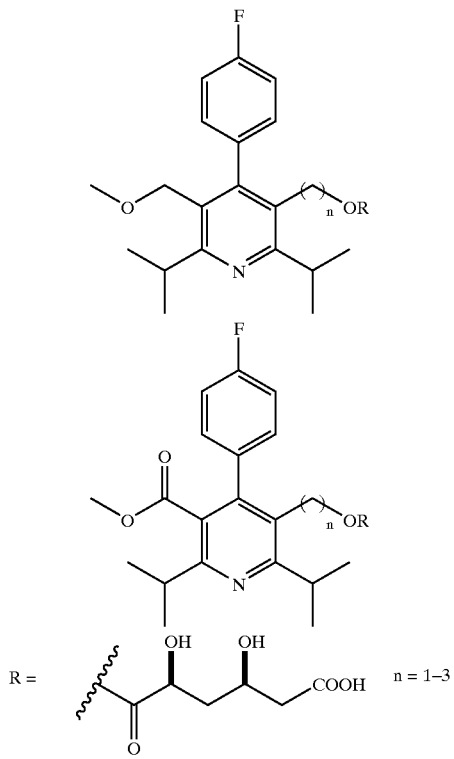

and salts thereof.

2. An inhibitor of HMG-CoA reductase having a structure selected from the group consisting of:

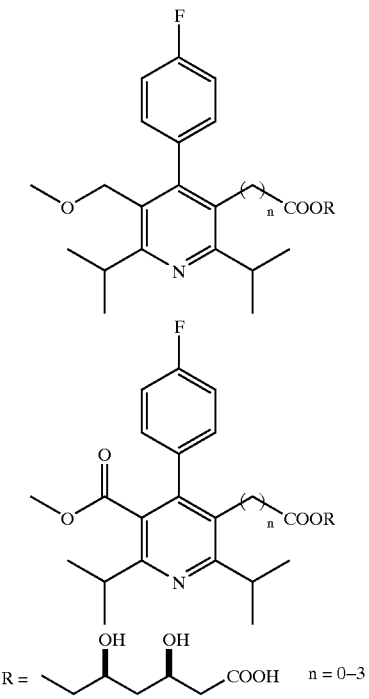

and salts thereof.

3. A pharmaceutical composition wherein said composition comprises a pharmaceutical carrier and a compound having a structure selected from the group consisting of:

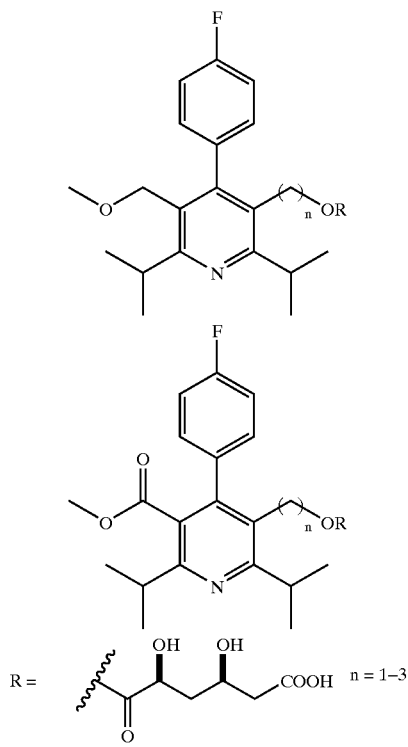

and salts thereof.

4. A pharmaceutical composition wherein said composition comprises a pharmaceutical carrier and a compound having a structure selected from the group consisting of:

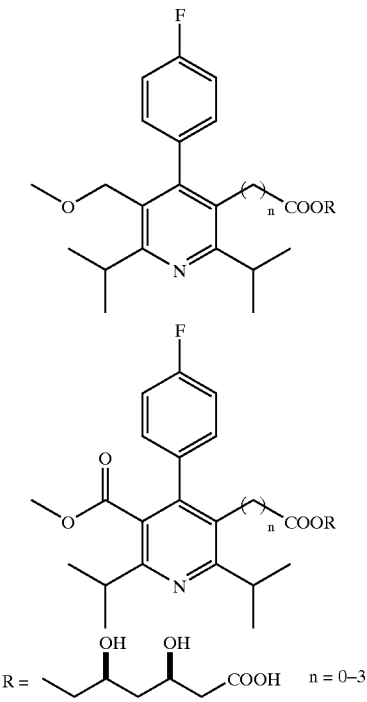

and salts thereof.

5. A method for inhibiting HMG-CoA reductase in an individual in need of such treatment wherein said method comprises administering to said individual a compound wherein said compound has a structure selected from the group consisting of:

$R = $ [structure with OH OH COOH, n = 1–3, ketone]

and salts thereof.

6. A method for inhibiting HMG-CoA reductase in an individual in need of such treatment wherein, said method comprises administering to said individual a compound, wherein said compound has a structure selected from the group consisting of:

[structures with COOR, n]

$R = $ [structure with OH OH COOH, n = 0–3]

7. The method, according to claim 5, wherein the individual is a human.

8. The method, according to claim 5, wherein said method is used to lower cholesterol levels.

9. The method, according to claim 6, wherein the individual is a human.

10. The method, according to claim 6, wherein said method is used to lower cholesterol levels.

* * * * *

UNITED STATES PATENT AND TRADEMARK OFFICE
CERTIFICATE OF CORRECTION

| | |
|---|---|
| PATENT NO. | : 6,951,877 B2 |
| APPLICATION NO. | : 10/624659 |
| DATED | : October 4, 2005 |
| INVENTOR(S) | : Druzgala et al. |

It is certified that error appears in the above-identified patent and that said Letters Patent is hereby corrected as shown below:

On the title page (75)
Inventors: Please add -- Jurg R. Pfister, Los Altos, CA (US) --.

Signed and Sealed this

Twelfth Day of September, 2006

JON W. DUDAS
*Director of the United States Patent and Trademark Office*